US009757255B2

(12) United States Patent
Caldwell et al.

(10) Patent No.: US 9,757,255 B2
(45) Date of Patent: *Sep. 12, 2017

(54) VACUUM PUMP SYSTEMS FOR PROSTHETIC LIMBS AND METHODS OF USING THE SAME

(71) Applicants: Northwestern University, Evanston, IL (US); U.S. Department of Veterans Affairs, Washington, DC (US)

(72) Inventors: Ryan J. Caldwell, Long Grove, IL (US); Andrew H. Hansen, Apple Valley, MN (US); Sean M. Wood, Hermosa Beach, CA (US); Wei Chen, Wilmette, IL (US); Regan A. Radcliffe, San Francisco, CA (US); Kevin A. Yngve, Chicago, IL (US); Bennett E. Kuhar, Concord Township, OH (US); Andrew J. Nelson, Chicago, IL (US); Eric Nickel, Brooklyn Park, MN (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,816

(22) Filed: Jun. 4, 2015

(65) Prior Publication Data
US 2015/0265436 A1 Sep. 24, 2015

Related U.S. Application Data

(62) Division of application No. 13/529,833, filed on Jun. 21, 2012, now Pat. No. 9,066,822.
(Continued)

(51) Int. Cl.
*A61F 2/80* (2006.01)
*A61F 2/68* (2006.01)
(Continued)

(52) U.S. Cl.
CPC .............. *A61F 2/80* (2013.01); *A61F 2/60* (2013.01); *A61F 2/68* (2013.01); *A61F 2/70* (2013.01);
(Continued)

(58) Field of Classification Search
CPC .. A61F 2/80; A61F 2/78; A61F 2/7812; A61F 2002/442; A61F 2002/7812; A61F 2002/5032; A61F 2002/742
See application file for complete search history.

(56) References Cited

U.S. PATENT DOCUMENTS 4,161,042 A 7/1979 Cottingham et al.
5,724,714 A 3/1998 Love
(Continued)

OTHER PUBLICATIONS

International Search Report and Written Opinion for PCT/US2012/043685 dated Sep. 21, 2012.

*Primary Examiner* — Bruce E Snow
(74) *Attorney, Agent, or Firm* — Cook Alex Ltd.

(57) ABSTRACT

Pump systems for use in suspension of a prosthetic device from a residual limb and methods of suspending a prosthetic device from a residual limb are disclosed. The pump systems include a mechanically activated pump having a first compression member coupled to a second compression member, a compressible bladder disposed between the first and second compression members, and coupling elements that engage and couple together the first and second compression members. The mechanically activated pump may be connected with an electrically activated pump within a fluid circuit of a hybrid pump system to provide vacuum engagement between a prosthetic device and a residual limb.

26 Claims, 14 Drawing Sheets

Related U.S. Application Data

(60) Provisional application No. 61/571,233, filed on Jun. 23, 2011.

(51) Int. Cl.
 *A61F 2/50* (2006.01)
 *A61F 2/60* (2006.01)
 *A61F 2/70* (2006.01)
 *A61F 2/74* (2006.01)
 *A61F 2/76* (2006.01)

(52) U.S. Cl.
 CPC . *A61F 2002/501* (2013.01); *A61F 2002/5073* (2013.01); *A61F 2002/607* (2013.01); *A61F 2002/608* (2013.01); *A61F 2002/6809* (2013.01); *A61F 2002/689* (2013.01); *A61F 2002/704* (2013.01); *A61F 2002/741* (2013.01); *A61F 2002/742* (2013.01); *A61F 2002/747* (2013.01); *A61F 2002/7655* (2013.01); *A61F 2002/802* (2013.01)

(56) References Cited

U.S. PATENT DOCUMENTS

| | | |
|---|---|---|
| 5,931,872 A | 8/1999 | Lohmann |
| 6,761,742 B2 | 7/2004 | Caspers |
| 7,025,792 B2 | 4/2006 | Collier |
| 7,744,653 B2 | 6/2010 | Rush et al. |
| 7,947,085 B2 | 5/2011 | Haines et al. |
| 8,007,543 B2 | 8/2011 | Martin |
| 8,308,816 B2 | 11/2012 | Slemker et al. |
| 9,066,822 B2 * | 6/2015 | Caldwell ............... A61F 2/80 |
| 2002/0099450 A1 | 7/2002 | Dean, Jr. et al. |
| 2005/0149202 A1 | 7/2005 | Schaffer et al. |
| 2005/0278039 A1 | 12/2005 | Nobbe |
| 2007/0055383 A1 | 3/2007 | King |
| 2007/0112439 A1 | 5/2007 | Panucialman |
| 2007/0213839 A1 | 9/2007 | Nachbar |
| 2008/0221706 A1 | 9/2008 | Scussel et al. |
| 2008/0269911 A1 | 10/2008 | Street et al. |
| 2009/0036998 A1 | 2/2009 | Finlinson et al. |
| 2009/0192619 A1 | 7/2009 | Martin et al. |
| 2009/0222105 A1 | 9/2009 | Clausen |
| 2010/0094432 A1 * | 4/2010 | Mackenzie ............... A61F 2/68 623/34 |
| 2010/0312360 A1 | 12/2010 | Caspers |
| 2011/0046748 A1 | 2/2011 | Martin et al. |
| 2011/0060421 A1 | 3/2011 | Martin et al. |
| 2011/0224802 A1 | 9/2011 | Finlinson et al. |
| 2012/0123559 A1 | 5/2012 | Mosler et al. |

* cited by examiner

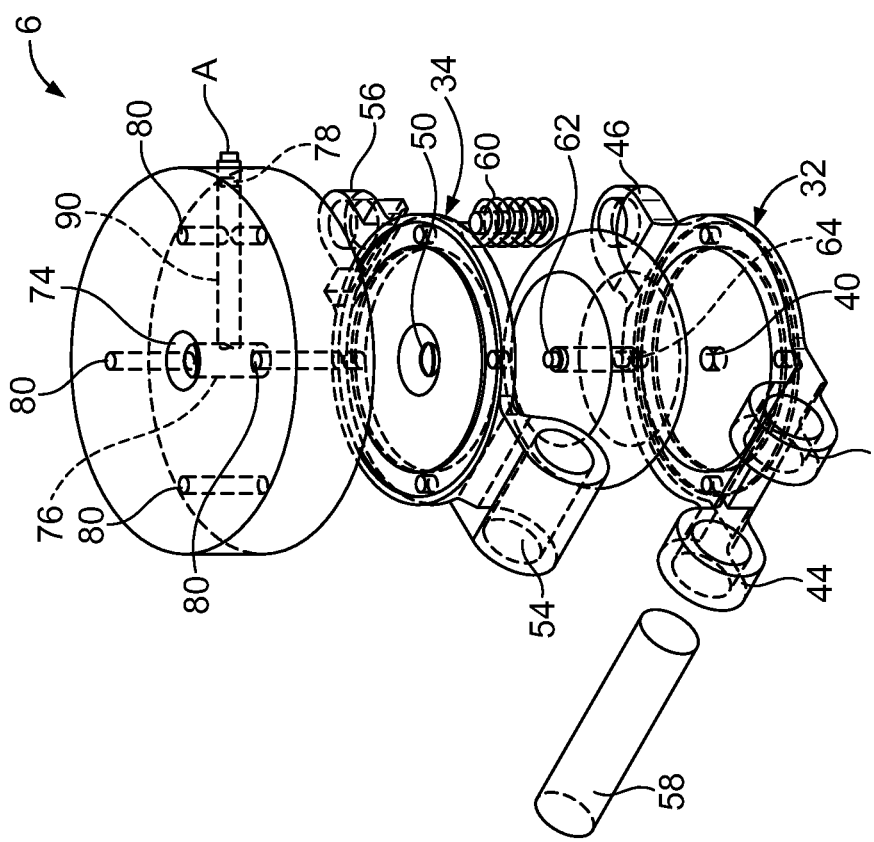
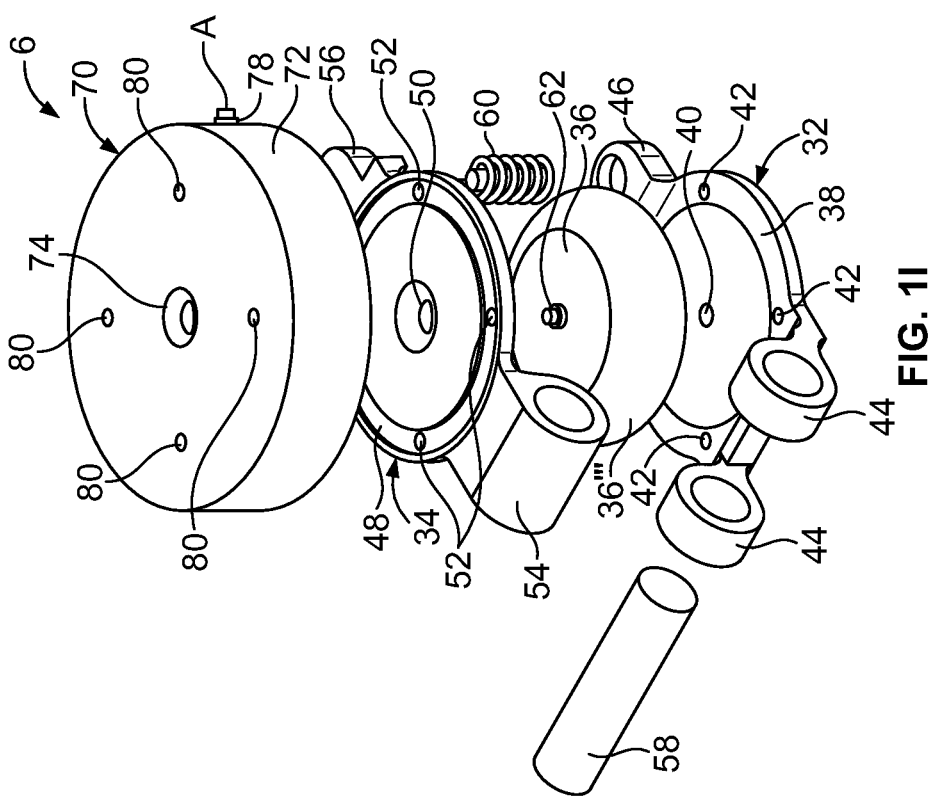

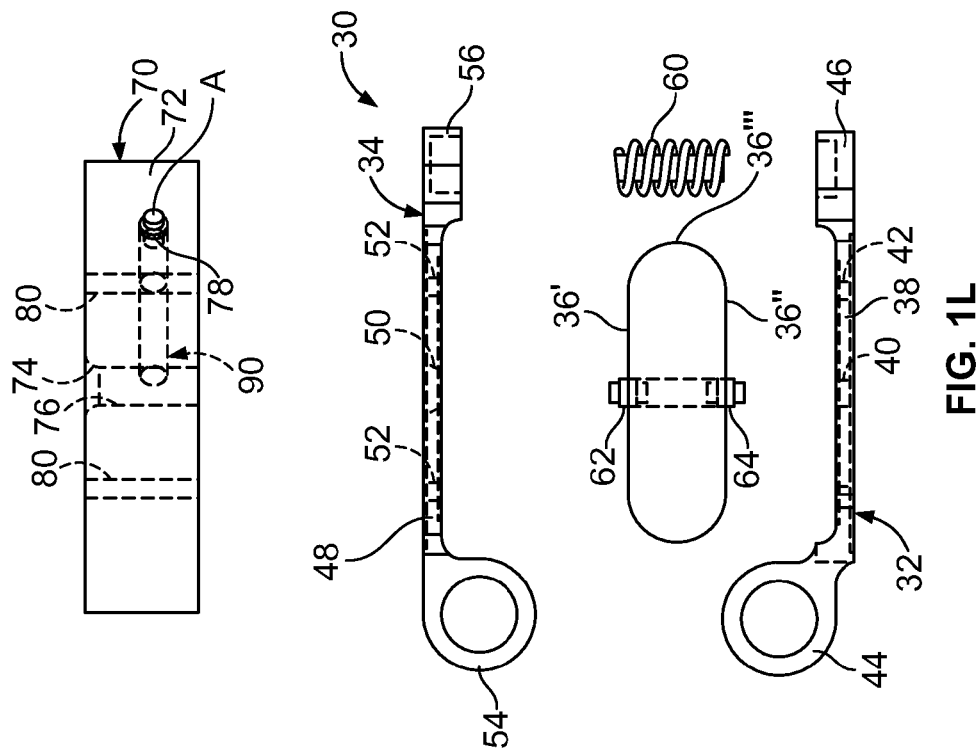
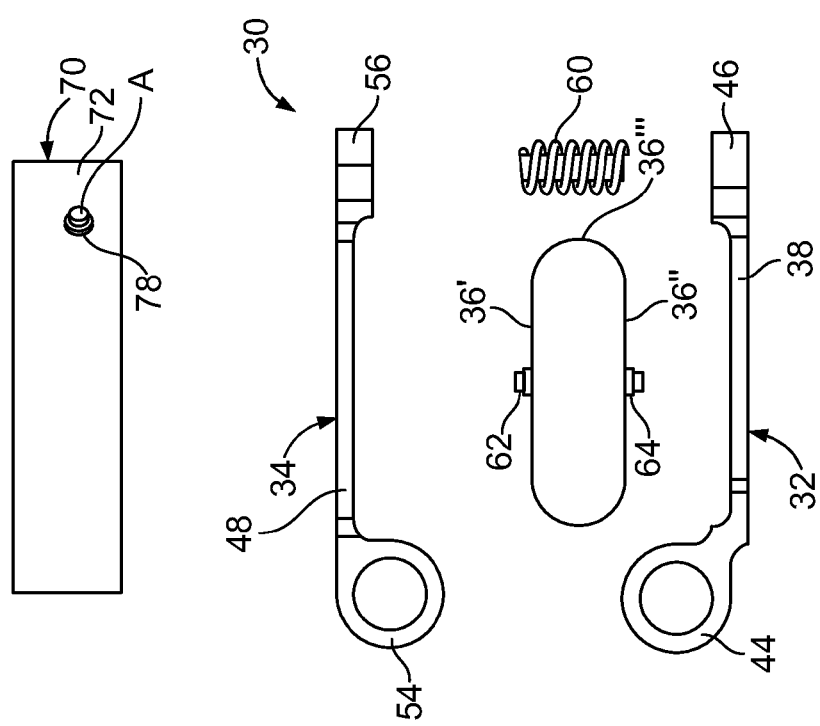
FIG. 1L
FIG. 1K

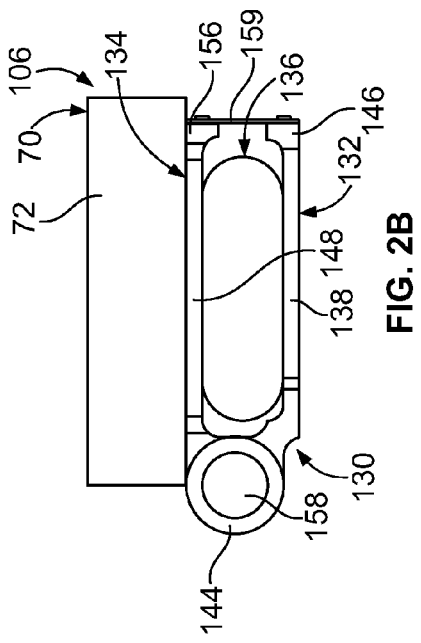
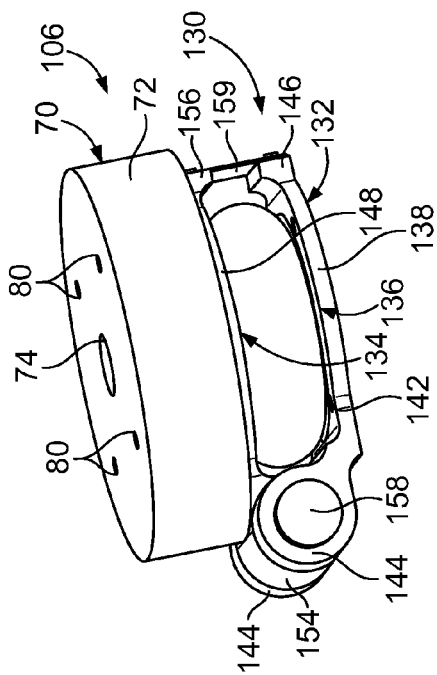
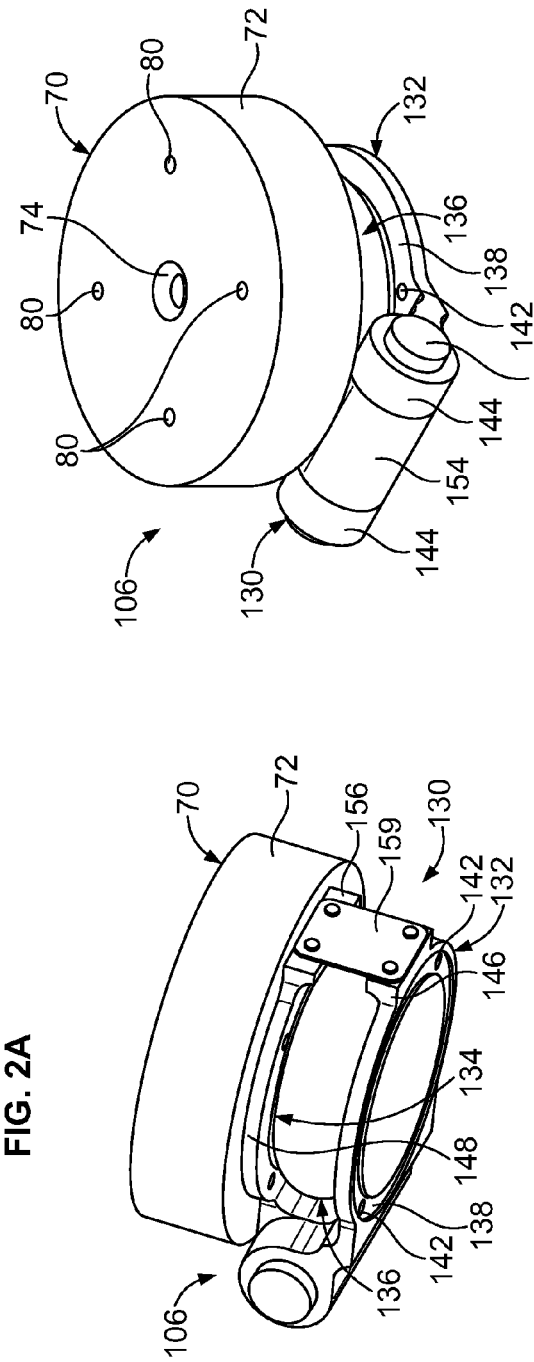

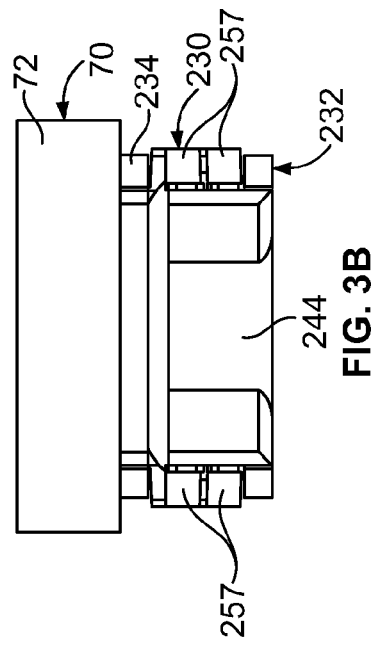
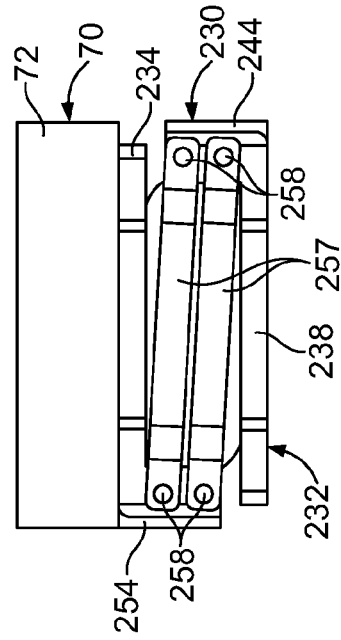
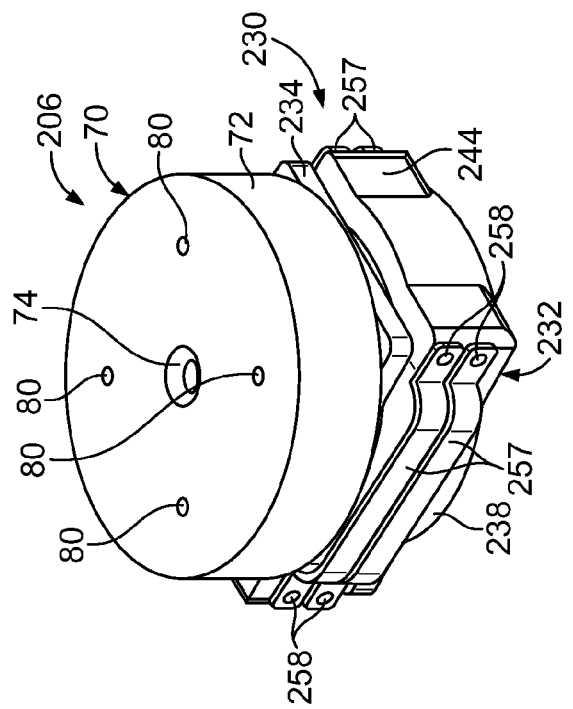

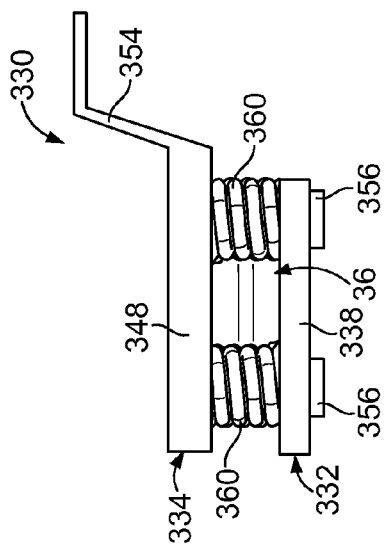
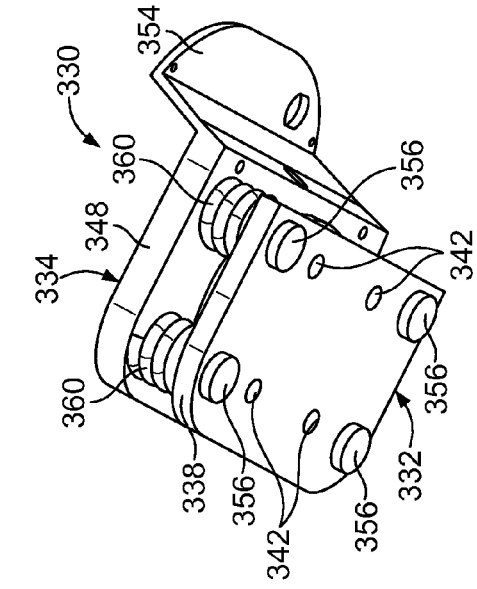
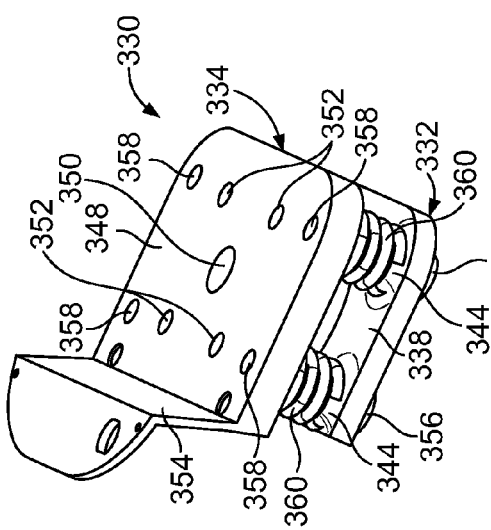

VACUUM PUMP SYSTEMS FOR PROSTHETIC LIMBS AND METHODS OF USING THE SAME

CROSS-REFERENCE TO RELATED APPLICATIONS

This application is a divisional application of co-pending U.S. patent application Ser. No. 13/529,833, filed Jun. 21, 2012, and further claims benefits and priority of U.S. Provisional Patent Application Ser. No. 61/571,233, filed Jun. 23, 2011, the disclosures of which are hereby incorporated by reference in their entirety.

CONTRACTUAL ORIGIN OF THE INVENTION

This invention was made with government support under W81XWH-10-1-0744 awarded by the U.S. Army Medical Research and Material Command and H133E080009 awarded by the National Institute on Disability and Rehabilitation Research (NIDDR). The government has certain rights in the invention.

BACKGROUND OF THE INVENTION

Field of the Invention

The present invention generally relates to suspension systems for prosthetic devices, and more particularly to vacuum pump systems for prosthetic limbs that include at least a mechanically activated pump.

Discussion of the Prior Art

Various systems have been developed for coupling a prosthetic device or prosthetic limb to a residual limb. The residual limb is connected to the prosthesis via a socket which receives and holds in place an end portion of the residual limb. Suspension is the mechanism that holds the socket to the residual limb. Vacuum is a form of suspension that uses a difference in atmospheric pressure to hold a socket to the residual limb. Liners help protect the residual limb tissue by providing cushioning and helping distribute the applied negative pressure in a uniform manner.

Vacuum pump technology is used to suspend the socket to the residual limb by creating a vacuum between the liner and the socket. The ability to maintain vacuum at a relatively consistent level can help avoid undesirable movement between the socket and the residual limb which improves comfort and avoids soft tissue damage.

Vacuum pumps fall into two categories, namely, mechanically activated or electrically activated. Electrically activated pumps tend to evacuate air more quickly, are able to monitor and adjust the vacuum pressure, and to automatically initiate pump operation if the vacuum pressure is not at least at a preselected threshold. However, electrically activated pumps include a small DC motor that requires a power source, such as disposable or rechargeable batteries. Electrically activated pumps also may generate undesirable noise.

Mechanically activated pumps use the walking motion of the user to create vacuum. One way pressure valves permit proper maintenance of vacuum pressure, without access to electricity. The necessary vacuum may be maintained indefinitely as long as there are no leaks in the system and/or the user walks occasionally. However, the mechanically activated pumps do not provide initial evacuation of air without effort, take longer to achieve operative vacuum levels, and typically need periodic motion to maintain appropriate vacuum levels. Mechanically activated pumps also tend to require a significant length for operation, as they typically operate by using a telescoping assembly. Depending on the number of parallel alignment elements involved, length can be important within a telescoping assembly, so as to provide adequate surface engagement to avoid binding. Mechanically activated pumps generally are configured for mounting below the knee because the pumps are too long to fit between the socket and the knee joint of the prosthetic limb, and as such, are not as well suited for transfemoral amputees.

Mechanically activated pumps also typically use a piston within a cylinder for pumping, or systems that include a flexible toroidal or ring-shaped reservoir or bladder that has a relatively large cylindrical telescopic tube running through the center, in place of a section of a lower limb pylon. The tube must be relatively large and of length sufficient to avoid binding, while withstanding the significant stresses encountered. In turn, the reservoir must be constructed to account for the large opening through the center.

For some users, such as military personnel with amputation who wish to return to active duty, there is an enhanced need to be able to maintain acceptable physical performance. An active soldier with amputation may be in the field for a prolonged period of time, with a need to maintain proper vacuum levels for suspension, while being without access to a power source for recharging of batteries. Thus, there exists a need for a compact, quiet, unobtrusive vacuum pump system with adjustable pressure and minimal battery recharging needs that will evacuate air from a cavity between a socket of a prosthetic limb and a residual limb.

The present invention addresses shortcomings in prior art vacuum pump systems for prosthetic limbs, while providing enhanced pumping systems that enable more flexible design and enhanced performance.

SUMMARY OF THE INVENTION

The purpose and advantages of the invention will be set forth in and apparent from the description and drawings that follow, as well as will be learned by practice of the claimed subject matter.

The present disclosure generally provides pump systems that include mechanically activated pumps having a lower profile design while still being able to provide vacuum within the desired range of 15 mmHg to 25 mmHg. The mechanically activated pumps utilize a bladder but do not require a large central opening for a tubular telescopic assembly. By avoiding use of such a central tubular telescopic assembly, the mechanically activated pumps of the present disclosure permit use of a relatively large diameter bladder having a greater volume and which requires less displacement to achieve adequate pumping capacity. Such pumps optionally permit location above or below the knee joint in a transfemoral prosthetic limb, or compact placement within a transtibial prosthetic limb.

The mechanically activated pumps of the present disclosure may utilize first and second compression members, with a compressible bladder disposed therebetween and any of a variety of coupling elements disposed about an outer perimeter of the compressible bladder. Thus, the compression members may be pivotally coupled in a configuration that permits angular displacement of a first compression member relative to a second compression member, or in a configuration that permits the first compression member to translate, maintaining a parallel relationship to the second compression member. Alternatively, the compression members may be coupled in a configuration that does not involve any pivotal connection, and permits the first compression member to translate relative to the second compression member.

To further enhance the performance of pump systems for suspension of a prosthetic limb, the present disclosure also provides pump systems that include an electrically activated pump, such as of the micro pump type utilized in exclusively electrical systems, thereby providing a modular hybrid system. A hybrid pump system may offer significant advantages, such as the desired rapid engagement upon initial donning of the prosthetic device, while not requiring solely battery power to evacuate air and to maintain appropriate vacuum levels. This may permit elongated intervals between charging of rechargeable batteries or battery packs, or between replacement of disposable batteries. A hybrid system also may provide for better optimization of the size and capacities of the components utilized, as the mechanically activated pump portion of a hybrid system need not be as concerned with the ability to rapidly establish initial evacuation solely via the mechanically activated pump, while the electrically activated pump is less likely to be cycled during the course of many activities that now will provide operation of a mechanically activated pump. Accordingly, depending on the length of the residual limb, it may be possible to implement a hybrid pump system of this disclosure within a system having a relatively short length, such that it could be located above the knee joint for a transfemoral amputee.

Thus, a hybrid system may utilize the respective strengths of mechanically and electrically activated pumps to achieve superior overall performance, while essentially also providing a redundant pump system to ensure at least adequate performance for the user. By utilizing a low profile design, the systems also permit placement above the knee for a transfemoral amputee, for direct interaction with a socket of a prosthetic device. The pump systems preferably have a height of about 1.5 inches or less, to permit positioning above the knee. It will be appreciated that the height may be more or less, depending on the configuration of mechanically activated pump, and whether or not the system includes an electrically activated pump, as well as its configuration. This, in turn, helps avoid many of the hindrances associated with below knee systems, while permitting an inline assembly that need not require external tubing.

Accordingly, in a first aspect, disclosed herein is a pump system for use in suspension of a prosthetic device from a residual limb. The pump system includes a mechanically activated pump having a first compression member coupled to a second compression member, a compressible bladder disposed between the first and second compression members, and coupling elements that engage and couple together the first and second compression members, wherein all of the coupling elements are disposed about an outer perimeter of the compressible bladder.

In a second aspect, disclosed herein is a method of suspending a prosthetic device from a residual limb. The method includes providing a prosthetic device having a socket that receives the residual limb. The method further includes providing a mechanically activated pump having a first compression member coupled to a second compression member, a compressible bladder disposed between the first and second compression members, and coupling elements engaging and coupling together the first and second compression members, wherein all of the coupling elements are disposed about an outer perimeter of the compressible bladder. The method also includes providing a fluid circuit in communication with the socket and the compressible bladder, the fluid circuit being configured to evacuate air from the socket when operating the mechanically activated pump, and operating the mechanically activated pump when the prosthetic device is used to walk.

In a third aspect, disclosed herein is hybrid pump system for use in suspension of a prosthetic device from a residual limb. The hybrid pump system includes a mechanically activated pump, an electrically activated pump, and the mechanically activated pump and electrically activated pump are connected within a fluid circuit that provides vacuum engagement between the prosthetic device and the residual limb.

It will be appreciated that the unique mechanically activated pumps disclosed herein provide advantageous configurations that permit low profile arrangements to be utilized in suspending a prosthetic device from a residual limb. It also will be appreciated from this disclosure that a mechanically activated pump may be connected to a fluid circuit that includes an electrically activated pump, so as to create a hybrid system for use in suspension of a prosthetic device from a residual limb. It is contemplated that various configuration may be utilized and the appended claims are not to be limited to the examples illustrated.

Thus, the present disclosure presents alternatives to the prior art mechanically activated pumps, as well as to systems that use only an electrically activated pump, where the prior art systems have proven to be less effective than desired.

It is to be understood that both the foregoing general description and the following detailed description are exemplary and provided for purposes of explanation only, and are not restrictive of the subject matter claimed. Further features and objects of the present disclosure will become more fully apparent in the following description of the preferred embodiments and from the appended claims.

BRIEF DESCRIPTION OF THE DRAWINGS

In describing the preferred embodiments, reference is made to the accompanying drawing figures wherein like parts have like reference numerals, and wherein:

FIG. 1I is an upper front perspective partially exploded view of the pump system shown in FIG. 1A.

FIG. 1J is an alternative view of that shown in FIG. 1I, showing a portion of the fluid circuit of the pump system shown in FIG. 1A.

FIG. 1K is a side partially exploded view of the pump system shown in FIG. 1A.

FIG. 1L is an alternative view of that shown in FIG. 1K, showing a portion of the fluid circuit of the pump system shown in FIG. 1A.

FIG. 2A is a side perspective view of a second example pump system for a prosthetic device.

FIG. 2B is a side view of the pump system shown in FIG. 2A

FIG. 2C is a lower rear perspective view of the pump system shown in FIG. 2A.

FIG. 2D is an upper front perspective view of the pump system shown in FIG. 2A.

FIG. 3A is an upper perspective view of a third pump system for a prosthetic device.

FIG. 3B is a front view of the pump system shown in FIG. 3A.

FIG. 3C is a side view of the pump system shown in FIG. 3A.

FIG. 4C is a rear view of the pump system shown in FIG. 4A.

FIG. 4D is a side view of the pump system shown in FIG. 4A.

FIG. 4E is an upper perspective view of the pump system shown in FIG. 4A.

FIG. 4F is a lower perspective view of the pump system shown in FIG. 4A.

It should be understood that the drawings are not to scale. While some details of a pump system for a prosthetic device, including details of fastening means and other plan and section views of the particular components, have not been included, such details are considered well within the comprehension of those of skill in the art in light of the present disclosure. It also should be understood that the present invention is not limited to the example embodiments illustrated.

DETAILED DESCRIPTION OF THE PREFERRED EMBODIMENTS

Referring generally to FIGS. 1A-4H, it will be appreciated that a vacuum pump system for use in suspension of a prosthetic device from a residual limb of the present disclosure generally may be embodied within numerous configurations of pump systems having a mechanically activated pump and/or a hybrid pump system having a mechanically activated pump and an electrically activated pump. Indeed, while acknowledging that all of the example configurations may include at least one of the example mechanically activated pumps, it is contemplated that a pump system may be incorporated into various prosthetic devices, such as transfemoral and transtibial prosthetic limbs.

Figure 1A:
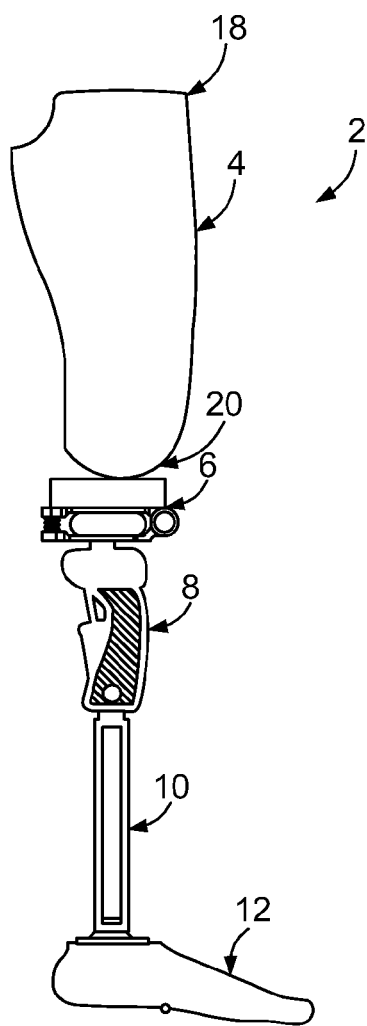
FIG. 1A is a simplified side view of a prosthetic device in the form of a prosthetic limb for a transfemoral amputee having a first example pump system that includes a mechanically activated pump, with the pump system also including an electrically activated pump, so as to provide a hybrid pump system.

FIG. 1A shows a simplified side view of a prosthetic device or limb 2 in the form of a prosthetic limb for a transfemoral amputee. The prosthetic device 2 generally includes a socket 4, a first example pump system 6, a knee joint 8, a pylon 10 and a prosthetic foot 12. The socket 4 has an upper end 18 that is open and is adapted to receive a transfemoral residual limb, with a lower end 20 that includes a port (not shown) in fluid communication with the pump system 6.

Figure 1B:
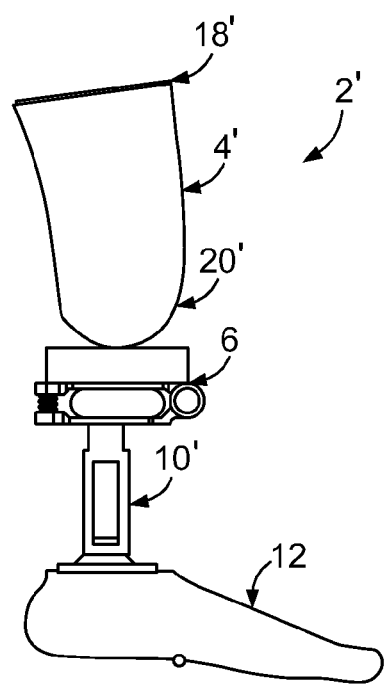
FIG. 1B is a simplified side view of a prosthetic device in the form of a prosthetic limb for a transtibial amputee having the pump system shown in FIG. 1A.
Figure 1C:
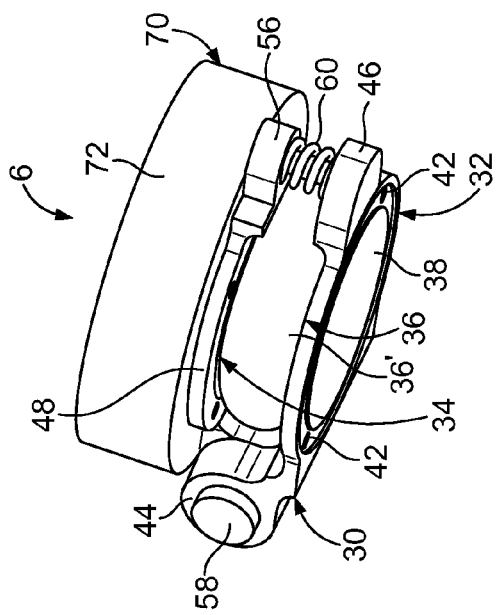
FIG. 1C is a side perspective view of the pump system shown in FIG. 1A.
Figure 1D:
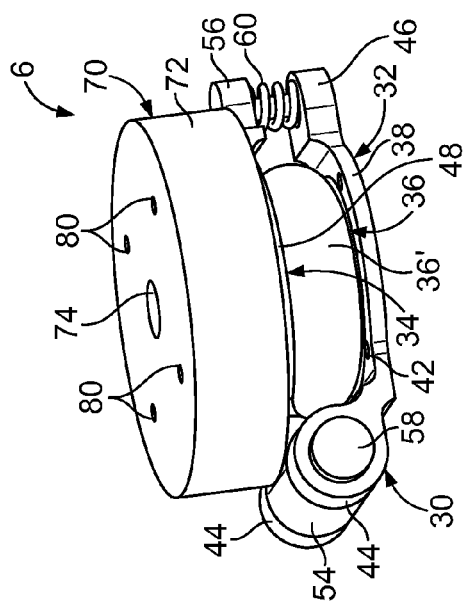
FIG. 1D is a lower rear perspective view of the pump system shown in FIG. 1A.
Figure 1E:
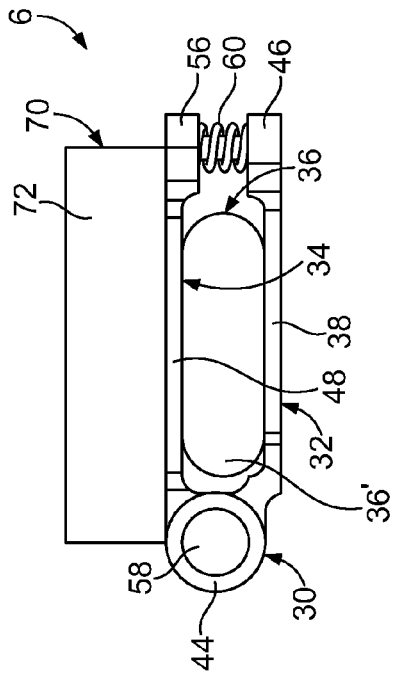
FIG. 1E is a side view of the pump system shown in FIG. 1A.

FIG. 1B incorporates somewhat similar components in showing a simplified side view of a prosthetic device or limb 2' in the form of a prosthetic limb for a transtibial amputee. The prosthetic device 2' generally includes a socket 4', the first example pump system 6, a pylon 10' and a prosthetic foot 12. The socket 4' has an upper end 18' that is open and is adapted to receive a transtibial residual limb, with a lower end 20' that includes a port (not shown) in fluid communication with the pump system 6.

There are numerous configurations of socket assemblies for suspension systems, some custom molded and constructed for direct contact with the skin of the residual limb, while others are intended to receive a residual limb that is covered with one or more liner components that prevent the skin from direct contact with the socket and exposure to vacuum pressure developed within the socket. It will be appreciated that the pump systems of the present disclosure could be configured for use in prosthetic devices with either type of socket, whether for use with transfemoral or transtibial residual limbs, with the components and specifications being appropriately matched to the desired vacuum pressure. Indeed, the specific construction and shape of the socket are not at issue, and depending on the particular configuration used, the port may be placed at various locations within the socket.

Although shown in simplified form, it will be understood that within a prosthetic device 2, 2', the lower end 20, 20' of the socket 4, 4' will include a mounting flange and associated fasteners, or other connective elements, for connection to the pump system 6 or to other intermediary components. Similarly, the upper end of the knee joint 8 or pylon 10' will be equipped for connection to the pump system 6, such as by having a mounting flange for a standard pyramid four bolt connector. It will be appreciated that the low profile, inline structure of the pump system 6 may be incorporated into a reduced package height, preferably although not necessarily of about 1.5 inches or less, which permits fluid connection of the pump system 6 to the lower end 20, 20' of the socket 4, 4', and may eliminate the need for external tubing.

Avoiding the use of external tubing can reduce the likelihood of interference or impedance of flexion of the knee, or the risk of getting caught on a protrusion.

A pump system 6 consistent with the first example may be seen in various views within FIGS. 1C-1L and includes at least a mechanically activated pump 30. As shown, the first example also includes an electrically activated pump 70, and the mechanically activated pump 30 and electrically activated pump 70 are connected within a fluid circuit 90 that is connected to and adapted to evacuate air from the socket 4, 4', thereby forming a particularly advantageous modular, hybrid pump system 6. The evacuation of air from the socket 4, 4', provides vacuum engagement between the prosthetic device 2, 2' and a respective transfemoral or transtibial residual limb. It also will be appreciated that with a pump system that includes a mechanically activated pump 30, the pump system alternatively could be configured for periodic use with a separate hand operated pump to establish initial air evacuation.

The hybrid pump system 6 of this first example provides a compact, low profile, inline structure. As may be seen in FIGS. 1C-1F and 1I-1L, the mechanically activated pump 30 of the first example pump system 6 includes a first compression member 32 coupled to a second compression member 34, with a compressible bladder 36 is disposed therebetween. The first and second compression members 32, 34 preferably are constructed of relatively light weight, generally rigid, suitable metals, such as aluminum alloys, titanium alloys, stainless steels or superalloys, or various plastics or composite materials. Depending on the environment to which a prosthetic device may be subjected, it may be desirable for the materials to be waterproof, sand-proof, and weather and corrosion resistant, although an outer pump system cover also may be employed to reduce the likelihood of intrusion of fluids or foreign matter.

The first compression member 32 includes a generally planar central body 38 having a central recess 40, spaced apart mounting apertures 42, and extensions in the form of hinge knuckles 44 that are opposite a flange 46. The mounting apertures 42 are configured to permit fasteners to pass therethrough for mounting to a standard pyramid four bolt connector at the upper end of a knee joint 8 or pylon 10', but it will be appreciated that alternative connective elements could be integrally formed into the first compression member for this or the other examples. The second compression member 34 includes a generally planar central body 48 having a central aperture 50, spaced apart mounting apertures 52, and an extension in the form of a hinge knuckle 54 that is opposite a flange 56. The first compression member 32 is coupled to the second compression member 34 via coupling elements that include a the hinge knuckles 44, 54 and a hinge pin 58 that pivotally engages the respective knuckles 44, 54, thereby making the first compression member 32 pivotally coupled to the second compression member 34. An optional spring assembly 60 extends between the respective flanges 46, 56 and biases the flanges toward a spaced apart position. Use of the spring assembly 60 may assist in providing consistent operation and feedback to the user.

While the coupling elements may be of a different configuration and size, the mechanically activated pump 30 should provide sufficient structural integrity and stability to maintain a consistent and predictable gait and resistance to torsional inputs, such as a twisting motion after planting a step. Also, it will be appreciated that the hinge or pivotal coupling is shown on the anterior or front side of the pump. While the hinge could be placed anteriorly or posteriorly, depending on the preference of particular prosthetists, placement anteriorly should cause the bladder to compress upon heel contact, providing some shock absorption, and movement of the pivots should mimic a desirable stance phase knee flexion.

The compressible bladder 36 may be particularly effective, while being of relatively short height because it has nearly continuous generally planar upper and lower surfaces 36', 36", which are connected to a radially bulging outer sidewall 36''' that defines an outer perimeter of the compressible bladder 36. This configuration of the compressible bladder 36 permits much greater capacity, and therefore potential efficiency, within a given overall diameter, when compared to a compressible bladder having an enlarged passage through the center to accommodate a tubular pylon-like telescopic structure. Locating the pump system 6 above the knee in a transfemoral configuration may permit a relatively large overall diameter, such as around 4 inches.

The compressible bladder 36 generally is an airtight, elastomeric body, and depending on the extent of the desired inherent rebound within the structure, and the anticipated environmental conditions, may be constructed of various rubbers, such as plasticized Halobutyl or polysulphide rubbers, plastics, such as ABS, PEEK or other polymers, Nylon, composites or other suitable materials. Also, depending on the selected material, the compressible bladder may be constructed by blow molding or other suitable manufacturing techniques.

While the compressible bladder 36 may be constructed of one or more materials and in a manner that will tend to expand or return to its original non-compressed state, thereby separating the first and second compression members 32, 34, the optional spring assembly 60 is intended to ensure rebound and expansion of the compressible bladder 36 during repeated hinged compression movements that occur during walking or isolated bouncing-type movements. Also, it will be appreciated that many configurations of compression members, compressible bladders and coupling elements may be utilized to couple a first compressible member to a second compressible member, and optional spring assemblies may include alternative spring forms, including for example, a leaf spring, or a coiled torsion spring having opposed arms and being incorporated with a hinge pin, or other suitable alternative structures.

The first and second compression members 32, 34 and compressible bladder 36 utilize a fluid circuit 90 to evacuate air from the socket 4, 4'. The compressible bladder 36 includes an intake valve 62 that communicates through the aperture 50 in the second compression member 34, and an output valve 64 that is vented to the atmosphere to expel air that has been evacuated from the socket 4, 4' by the pump system 6.

In the first example, the electrically activated pump 70 is positioned inline with and connected to the second compression member 34 of the mechanically activated pump 30. As may be seen in a simplified manner in FIGS. 1L and 1J, the electrically activated pump 70 includes a housing 72 having an inlet valve 74 in communication with a central passage 76 therethrough for fluid connection to the socket 4, 4', and an output valve 78 that is vented to the atmosphere to expel air that has been evacuated from the socket 4, 4' by the pump system 6. The housing 72 also includes passages 80 therethrough that are aligned with the mounting apertures 52 in the second compression member 34 and together receive fasteners (not shown) that provide mechanical connection of the mechanically activated pump 30 and electrically activated pump 70 to a suitable mounting flange (not shown) at the lower end 20, 20' of a socket 4, 4'. It will be appreciated that the electrically activated pump may be equipped with alternative valving and operative features, as desired. Also, the housing of the electrically activated pump could be configured to be integrated into the lower end of a socket.

Figure 1G:
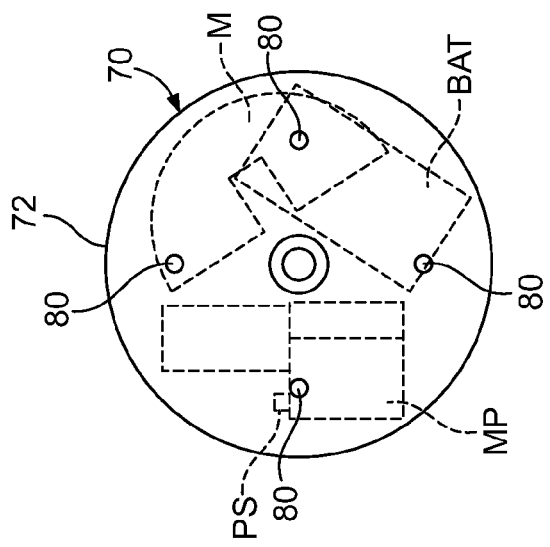
FIG. 1G is simplified top view of a layout of major components within the electrically activated pump of the pump system shown in FIG. 1A.
Figure 1H:
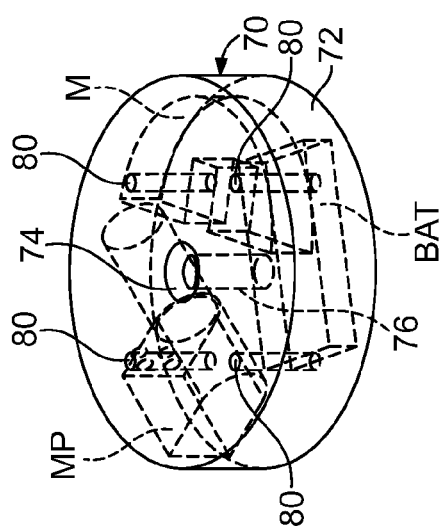
FIG. 1H is further simplified upper perspective view of a layout of major components within the electrically activated pump of the pump system shown in FIG. 1A.
Figure 1F:
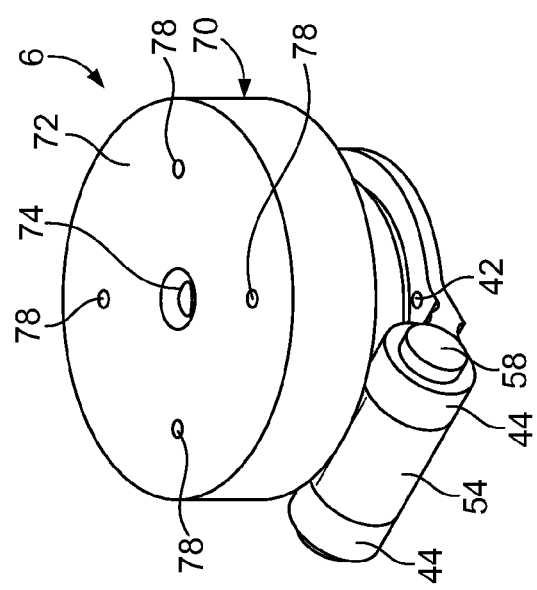
FIG. 1F is an upper front perspective view of the pump system shown in FIG. 1A.
Figure 1M:
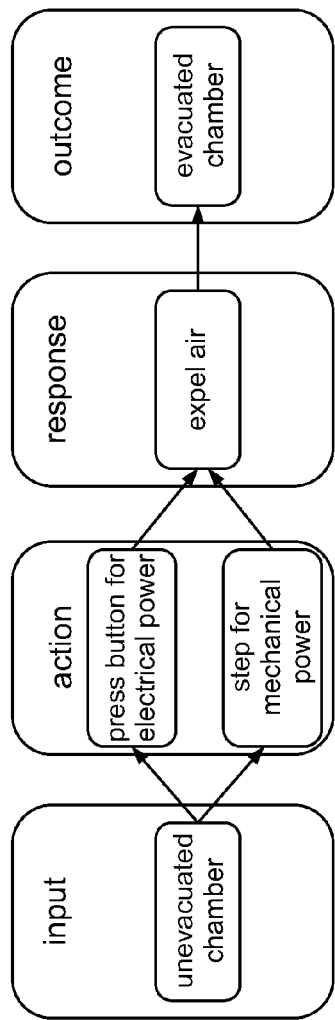
FIG. 1M is a schematic view of the process involved in using the pump system shown in FIG. 1A.
Figure 1N:
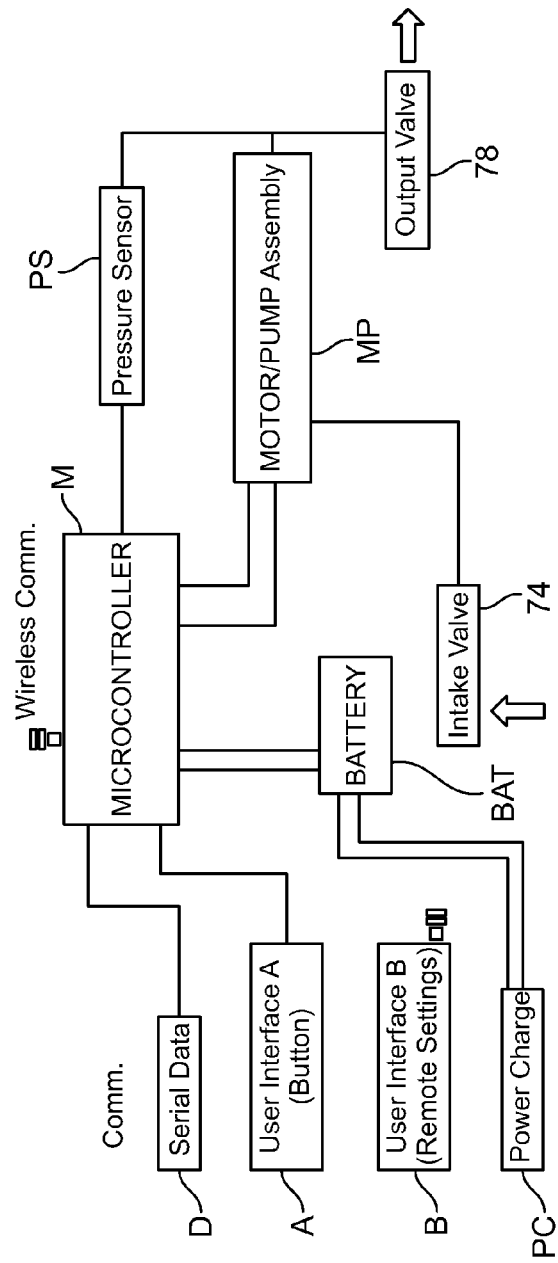
FIG. 1N is a schematic view of the control system for the pump system shown in FIG. 1A.

As may be appreciated in FIGS. 1G, 1H and 1N, the electrical components of the electrically activated pump 70 are shown in a simple layout and with a functional schematic to show the basic function and connection configuration. It will be appreciated that the components may be configured and connected in fluid communication by conventional means, such as by suitable tubing, and/or may be configured and connected electrically by conventional means, such as by suitable wires, leads or other circuitry, so as to meet the needs and satisfy the design specifications and constraints within of a particular implementation. In this first example, within the housing 72 of the electrically activated pump 70 is a microcontroller M that includes a circuit board and is connected to a motorized pump MP, a pressure sensor PS, and a battery BAT. A user interface A, in the form of an on/off button, is located in conjunction with the output valve 78 and is connected to the microcontroller M. An optional serial data port D may be utilized to interact with the microcontroller M, such as to track and record the operating conditions of the pump system 6, for diagnostic and historical monitoring purposes.

A further user interface B, such as in the form of a wireless remote control device, a personal data assistant device, a laptop or tablet computer, a cell phone or other wireless apparatus, may be utilized to interact with the microcontroller M to input particular settings that are associated with performance parameters, such as the minimum and maximum vacuum pressures between which the system will operate, the battery charge level at which a warning light or alarm may be emitted, or to adjust other parameters that would be desirable to control. The user interface B also may be used to display information associated with the present status of the system, such as the current vacuum pressure level, battery charge level, or predictive information, such as the battery life remaining or time interval until the next regular maintenance is recommended. The pump system 6 may include warning lights or alarms that may be connected to the housing 72, or embodied within a user interface B, to alert a user to important information.

The battery BAT preferably is rechargeable, such as by direct or indirect connection to a power charge device PC. It further is desirable that the battery BAT be replaceable, so as to permit one or more spare, charged batteries to be utilized during periods of extended use away from a power recharging source. It will be appreciated that the battery BAT may simply be of a disposable type, or that there could be an interface to permit interchangeability between a rechargeable battery and a disposable battery, based on the convenience and circumstances faced by the user.

It will be appreciated that the pump system 6 presents a hybrid, modular system that can be utilized in a number of ways. A high level schematic is provided in FIG. 1M to show that when the residual limb of a user has been received in a socket 4, 4', the user is faced with an input that essentially could be considered an unevacuated chamber. The user then may take one of two actions, namely, first to press a button, such as user interface button A on the housing 72, or on a user interface B, such as a remote control, to provide electrical power to engage the electrically activated pump 70, or second to step with the prosthetic limb 2, 2' to provide mechanical power to the mechanically activated pump 30.

The two different actions both cause the pump system 6 to provide a response by which air is expelled to the atmosphere, resulting in an outcome by which the chamber between the socket 4, 4' and the residual limb changes to an evacuated chamber.

Thus, the mechanically activated pump 30 or the electrically activated pump 70 may be used to evacuate air from the socket 4, 4', with the understanding that either pump may be used exclusively, if need be. However, maximum comfort and convenience can be achieved by first utilizing the electrically activated pump 70 to establish rapid initial evacuation, and thereafter the user may rely on the mechanically activated pump 30, if the user is actively moving, such as walking, running or able to impose at least a bouncing motion on the prosthetic limb 2, 2', or if the user happens to be inactive at a time when further evacuation of air is needed, the monitoring system within the electrically activated pump 70 may automatically engage the motorized pump MP to reestablish an acceptable vacuum pressure.

Figure 1O:
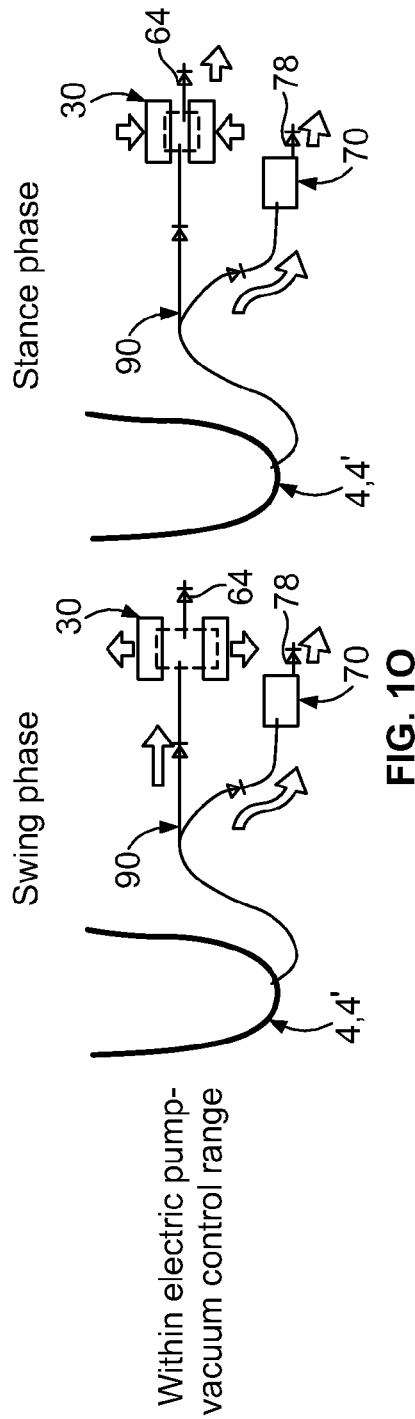
FIG. 1O is a schematic view of operation of the pump system shown in FIG. 1A when the electrically activated pump and the mechanically activated pump are in operation.

FIG. 1O provides a schematic representation of the pump system 6 when a user is walking and the pump system 6 is within an electrical pump-vacuum control range. Thus, within a swing phase, the first and second compressible members 32, 34 move away from each other, allowing the compressible bladder 36 to expand and draw air from the socket 4, 4'. Meanwhile, the electrically activated pump 70 may draw air from the socket 4, 4' and expel the air to the atmosphere through the output valve 78. Within the stance phase, the compression member 32 pivots relative to the compression member 34 to compress the compressible bladder 36, expelling the air previously withdrawn from the socket 4, 4', while the electrically activated pump 70 is able to continue to operate in the same manner as during the swing phase.

Figure 1P:
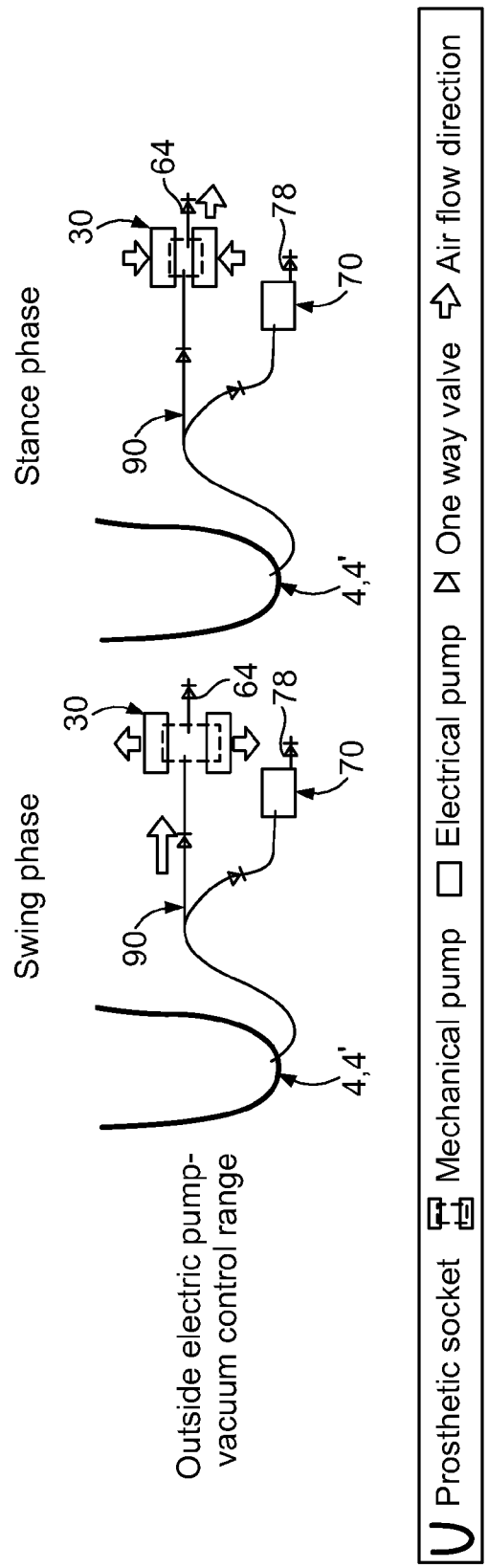
FIG. 1P is a schematic view of operation of the pump system shown in FIG. 1A when only the mechanically activated pump is in operation.

FIG. 1P provides a schematic representation of the pump system 6 when a user is walking and the pump system 6 is outside of an electrical pump-vacuum control range. While the schematic represents portions of the fluid circuit 90 as elongated lines, it will be appreciated that the connections between components may be direct, or may be by tubing, and that tubing could be used in a configuration of a prosthetic device having a socket 4 for a transfemoral residual limb, with a pump system 6 positioned below the knee joint. Within the swing phase shown in FIG. 1P, the first and second compressible members 32, 34 again move away from each other, allowing the compressible bladder 36 to expand and draw air from the socket 4, 4'. Meanwhile, the electrically activated pump 70 is not energized, to save battery charge. Within the stance phase, the compression member 32 pivots relative to the compression member 34 to compress the compressible bladder 36, expelling the air previously withdrawn from the socket 4, 4'.

From the foregoing description, it will be appreciated that a method of suspending a prosthetic device 2, 2' from a residual limb is provided herein. The method includes providing a prosthetic device 2, 2' having a socket 4, 4' that receives the residual limb. The method further includes providing a mechanically activated pump 30 having a first compression member 32 coupled to a second compression member 34, a compressible bladder 36 disposed between the first and second compression members 32, 34. The coupling elements include the hinge knuckles 44, 54 and the hinge pin 58 which engages and couples together the first and second compression members 32, 34, wherein all of the coupling elements are disposed about an outer perimeter that is defined by the sidewall 36''' of the compressible bladder 36, such that the coupling elements are at or beyond the outer perimeter of the compressible bladder 36. The method also includes providing a fluid circuit 90 in communication with the socket 4, 4' and the compressible bladder 36, the fluid circuit 90 being configured to evacuate air from the socket 4, 4' when operating the mechanically activated pump 30. Operation of the mechanically activated pump 30 occurs when the prosthetic device 2, 2' is used to walk.

Turning to FIGS. 2A-2F, a second example pump system 106 is disclosed for use in a prosthetic device, such as the prosthetic devices 2, 2'. The pump system 106 is quite similar to the first example pump system 6, but varies somewhat in the mechanically activated pump 130 that replaces the mechanically activated pump 30. However, the second example pump system 106 also includes at least a mechanically activated pump 130, and is equipped with an electrically activated pump 70. The mechanically activated pump 130 and electrically activated pump 70 are connected within a fluid circuit that is similar to the fluid circuit 90 and is connected to and adapted to evacuate air from the socket 4, 4', thereby forming a particularly advantageous hybrid pump system 106. The evacuation of air from the socket 4, 4', provides vacuum engagement between the prosthetic device 2, 2' and a respective transfemoral or transtibial residual limb.

The hybrid pump system 106 similarly provides a compact, low profile, inline structure, where the mechanically activated pump 130 includes a first compression member 132 coupled to a second compression member 134, which preferably are constructed of materials similar to those mentioned with respect to the first example pump system 6. A compressible bladder 136 is disposed between the first and second compression members 132, 134.

The first compression member 132 includes a generally planar central body 138 having a central recess 140, spaced apart mounting apertures 142, and extensions in the form of hinge knuckles 144 that are opposite a flange 146. The second compression member 134 includes a generally planar central body 148 having a central aperture 150, spaced apart mounting apertures 152, and an extension in the form of a hinge knuckle 154 that is opposite a flange 156. The first compression member 132 is coupled to the second compression member 134 via coupling elements that include a the hinge knuckles 144, 154 and a hinge pin 158 that pivotally engages the respective knuckles 144, 154, thereby making the first compression member 132 pivotally coupled to the second compression member 134. An optional strap 159 is connected, such as by rivets, screws or other fasteners, to the respective flanges 146, 156, extends between them and limits the pivotal travel of the first compression member 132 relative to the second compression member 134. In this second example pump system 106, an optional spring assembly 160 extends through a central opening 176 in the compressible bladder 136 between and biases the respective bodies 138, 148 toward a spaced apart position. It will be appreciated that the optional spring assembly 160 also would not be needed if the strap 159 alternatively incorporated a spring element.

The compressible bladder 136 may be particularly effective, while being of relatively short height because it has nearly continuous generally planar upper and lower surfaces 136', 136", which are connected to a radially bulging outer sidewall 136''' that defines an outer perimeter of the compressible bladder 136. As with the first example pump system 6, the coupling elements of the second pump system 106 are disposed about the outer perimeter of the compressible bladder 136. This configuration of the compressible bladder 136 permits much greater capacity within a given overall diameter, when compared to a compressible bladder having an enlarged passage through the center to accommodate a tubular pylon-like telescopic structure. The compressible bladder 136 generally is elastomeric and may be constructed of materials similar to those mentioned above with respect to the first example pump system 6.

While the compressible bladder 136 may be constructed of one or more materials and in a manner that will tend to expand to a non-compressed state, thereby separating the first and second compression members 132, 134, the optional spring assembly 160 is intended to ensure rebound and expansion of the compressible bladder 136 during repeated hinged compression movements that occur during walking or isolated bouncing-type movements. Also, it will be appreciated that many configurations of compression members, compressible bladders and coupling elements may be utilized to couple a first compressible member to a second compressible member, and optional spring assemblies may include alternative spring forms, such as are mentioned above with respect to the first example pump system 6.

The first and second compression members 132, 134 and compressible bladder 136 utilize a fluid circuit 190 to evacuate air from the socket 4, 4'. The fluid circuit 190 is similar to the fluid circuit 90 of the first example pump system 6, but the compressible bladder 136 incorporates an intake valve (not shown) that communicates through the aperture 150 in the second compression member 134, and an output valve (not shown) that is vented to the atmosphere to expel air that has been evacuated from the socket 4, 4' by the pump system 106.

In the second example, the electrically activated pump 70 is positioned inline with and connected to the second compression member 134 of the mechanically activated pump 130. As shown in a simplified manner, the electrically activated pump 70 is essentially the same as that shown in the first example pump system 6 and operates in the same way. The housing 72 of the electrically activated pump 70 includes passages 80 therethrough that are aligned with the mounting apertures 152 in the second compression member 134 and together receive fasteners (not shown) that provide mechanical connection of the mechanically activated pump 130 and electrically activated pump 70 to a suitable mounting flange (not shown) at the lower end 20, 20' of a socket 4, 4'.

Figure 2F:
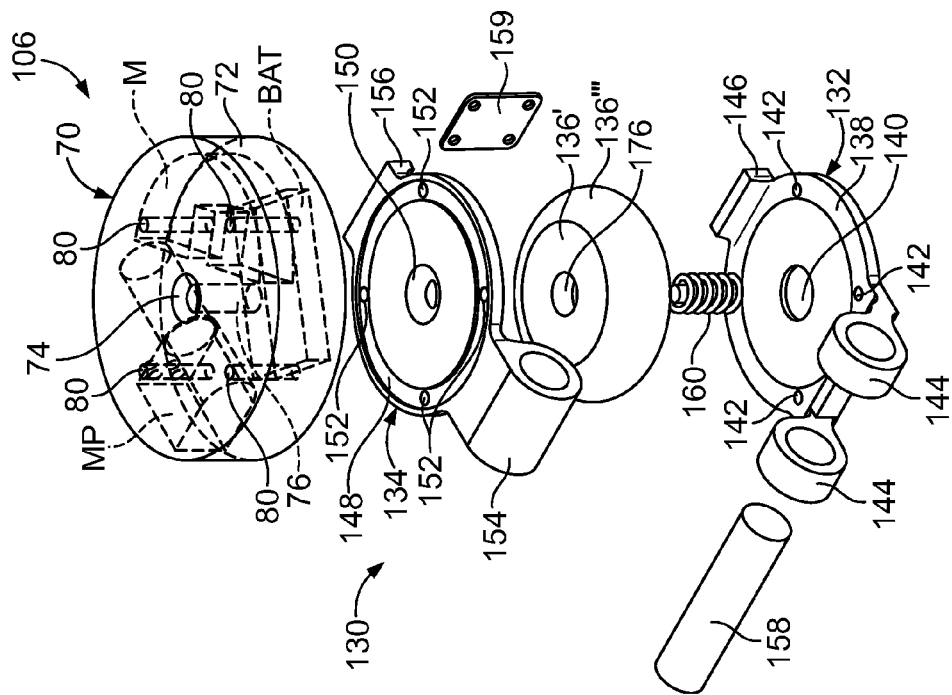
FIG. 2F is an alternative view of that shown in FIG. 2E, showing view of a layout of major components within the electrically activated pump of the pump system shown in FIG. 2E.
Figure 2E:
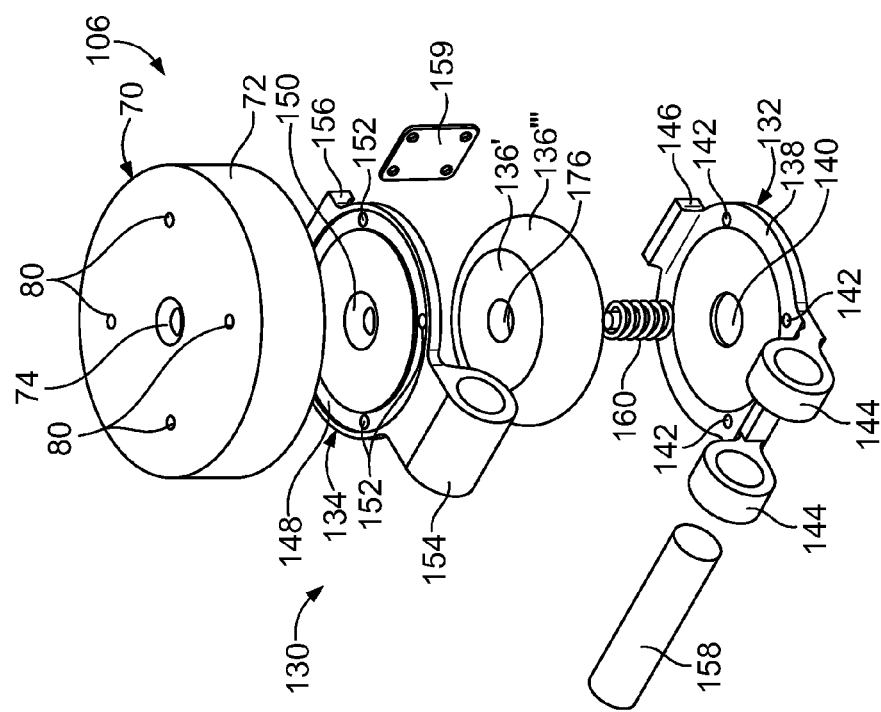
FIG. 2E is an upper front perspective partially exploded view of the pump system shown in FIG. 2A.

As may be best appreciated in FIG. 2F, the electrical components of the electrically activated pump 70 are shown in a simple layout, and it will be appreciated that the components may be configured and connected in a manner similar to that discussed above with respect to the first example pump system 6. The pump system 106 also may utilize similar user interfaces, operations and methods of use to those described above with respect to the schematic diagrams provided for the first example pump system 6.

Turning to FIGS. 3A-3E, a third example pump system 206 is disclosed for use in a prosthetic device, such as the prosthetic devices 2, 2'. The pump system 206 is somewhat similar to the second example pump system 106, but varies in the mechanically activated pump 230 that replaces the mechanically activated pump 130. However, the third example pump system 206 also includes at least a mechanically activated pump 230, and is equipped with an electrically activated pump 70 that is similar to that used in the first example pump system 6. The mechanically activated pump 230 and electrically activated pump 70 are connected within a fluid circuit that is similar to the fluid circuit 90 and is connected to and adapted to evacuate air from the socket 4, 4', thereby forming a particularly advantageous hybrid pump system 206. The evacuation of air from the socket 4, 4', provides vacuum engagement between the prosthetic device 2, 2' and a respective transfemoral or transtibial residual limb.

The hybrid pump system 206 similarly provides a compact, low profile, inline structure, where the mechanically activated pump 230 includes a first compression member 232 coupled to a second compression member 234, which preferably are constructed of materials similar to those mentioned with respect to the first example pump system 6. A compressible bladder 236 is disposed between the first and second compression members 232, 234.

The first compression member 232 includes a generally planar central body 238 having a central recess (not shown), spaced apart mounting apertures 242, and an extension 244 that is generally perpendicular to the central body 238 and has a pair of parallel bores 246 extending therethrough. The second compression member 234 includes a generally planar central body 248 having a central aperture 250, spaced apart mounting apertures 252, and an extension 254 that is generally perpendicular to the central body 248 and has a pair of parallel bores 256 extending therethrough. The respective pairs of parallel bores 246, 256 are parallel to each other and each bore is aligned with a further bore 255 through an end of a respective parallel upper or lower link 257. Pairs of pivot pins 258 are received by the respective pairs of bores 246, 256 in the first and second compression members 232, 234, and are pivotally connected to the bores 255 at the ends of the links 257.

The parallel links 257 permit the first and second compression members 232, 234 to be pivotally coupled to each other, but form a four bar linkage that also causes the first compression member 232 to translate toward and away from the second compression member 234, while maintaining a relative parallel orientation of the generally planar central bodies 238, 248. This compact, low profile configuration presents a further alternative that may utilize the same shorter height, yet higher capacity compressible bladder 136 that is used in the second example pump system 106. Accordingly, the compressible bladder 136 is disposed between the first and second compression members 232, 234, and utilizes an optional spring assembly 160 that extends through a central opening 176 in the compressible bladder 136 and assists in biasing the respective central bodies 238, 248 toward a spaced apart position. It will be appreciated that the coupling elements include the extensions 244, 254, the pivot pins 258 and the links 257.

The compressible bladder 136 may be particularly effective, while being of relatively short height because it has nearly continuous generally planar upper and lower surfaces 136', 136", which are connected to a radially bulging outer sidewall 136''' that defines an outer perimeter of the compressible bladder 136. In this configuration, as with the prior examples, the coupling elements are disposed generally outside of or about the outer perimeter of the compressible bladder 136. This permits much greater capacity within a given overall diameter, when compared to a compressible bladder having an enlarged passage through the center to accommodate a tubular pylon-like telescopic structure. The compressible bladder 136 generally is elastomeric and may be constructed of materials similar to those mentioned above with respect to the first example pump system 6. The first and second compression members 232, 234 and compressible bladder 136 utilize a fluid circuit that is the same as the fluid circuit 190 in the second example pump system to evacuate air from the socket 4, 4'.

While the compressible bladder 136 may be constructed of one or more materials and in a manner that will tend to expand to a non-compressed state, thereby separating the first and second compression members 232, 234, the optional spring assembly 160 is intended to ensure rebound and expansion of the compressible bladder 136 during repeated hinged compression movements that occur during walking or isolated bouncing-type movements. Also, it will be appreciated that many configurations of compression members, compressible bladders and coupling elements may be utilized to couple a first compressible member to a second compressible member, and optional spring assemblies may include alternative spring forms, such as are mentioned above with respect to the first example pump system 6.

In the third example, the electrically activated pump 70 is positioned inline with and connected to the second compression member 234 of the mechanically activated pump 230. As shown in a simplified manner, the electrically activated pump 70 is essentially the same as that shown in the first and second example pump systems 6, 106 and operates in the same way. The housing 72 of the electrically activated pump 70 includes passages 80 therethrough that are aligned with the mounting apertures 252 in the second compression member 234 and together receive fasteners (not shown) that provide mechanical connection of the mechanically activated pump 230 and electrically activated pump 70 to a suitable mounting flange (not shown) at the lower end 20, 20' of a socket 4, 4'.

Figure 3E:
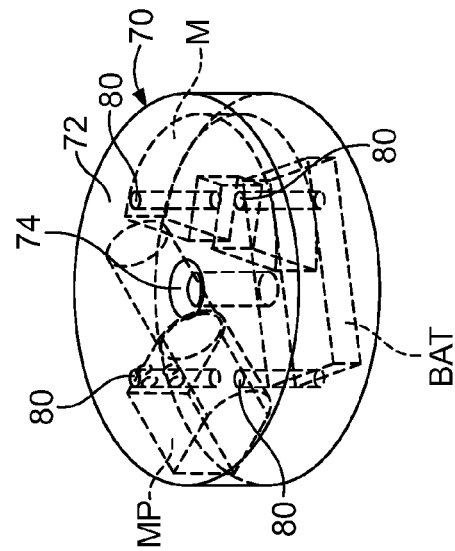
FIG. 3E is a simplified upper perspective view of a layout of major components within the electrically activated pump of the pump system shown in FIG. 3A.
Figure 3D:
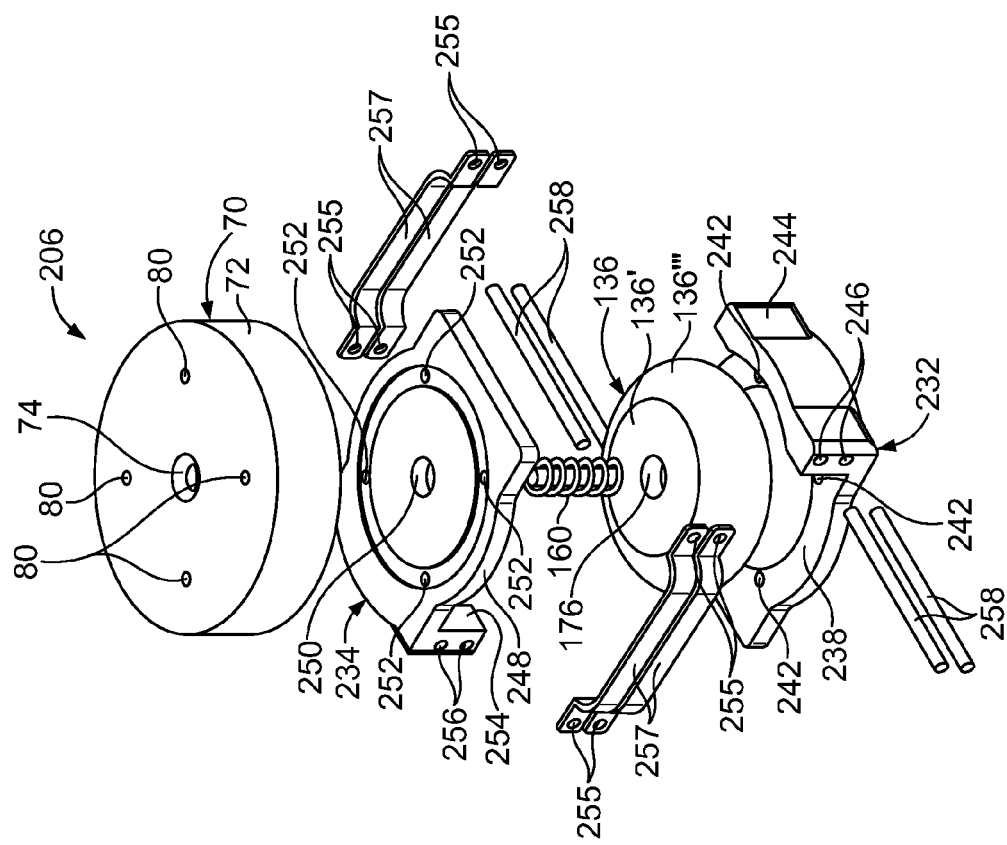
FIG. 3D is an upper front perspective partially exploded view of the pump system shown in FIG. 3A.

A simple schematic representation of the layout of the electrical components of the electrically activated pump 70 was previously provided with respect to the first example pump system 6, but is included again for convenience in FIG. 3E. Accordingly, it will be appreciated that the components of the third example pump system 206 may be configured and connected in a manner similar to that discussed above with respect to the first example pump system 6. The pump system 206 also may utilize similar user interfaces, operations and methods of use to those described above with respect to the schematic diagrams provided for the first example pump system 6. It further will be appreciated that the linkage and first and second compression members 232, 234 that provide parallel relative displacement, with a compressible bladder 136 therebetween, may achieve advantages over pumps utilized in other contexts and configurations.

Figure 4A:
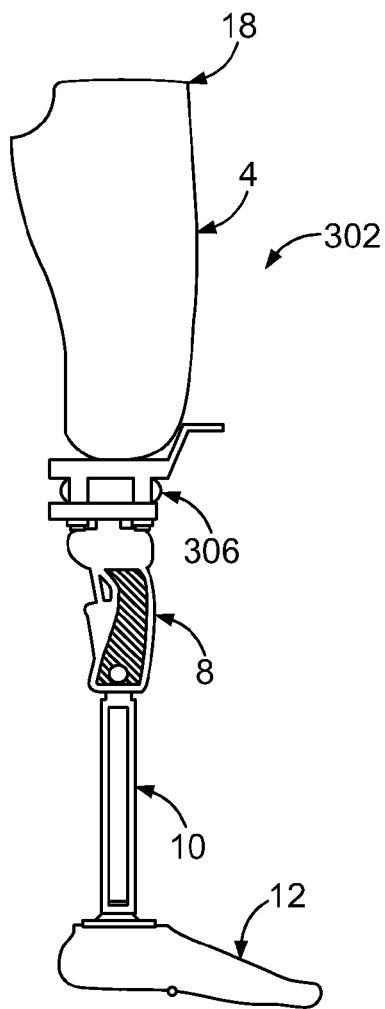
FIG. 4A is a simplified side view of a prosthetic device in the form of a prosthetic limb for a transfemoral amputee having a fourth example pump system that includes a mechanically activated pump.
Figure 4B:
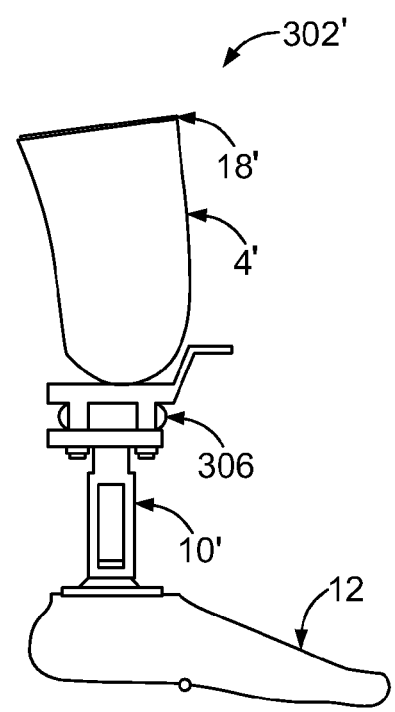
FIG. 4B is a simplified side view of a prosthetic device in the form of a prosthetic limb for a transtibial amputee having the pump system shown in FIG. 4A.
Figure 4H:
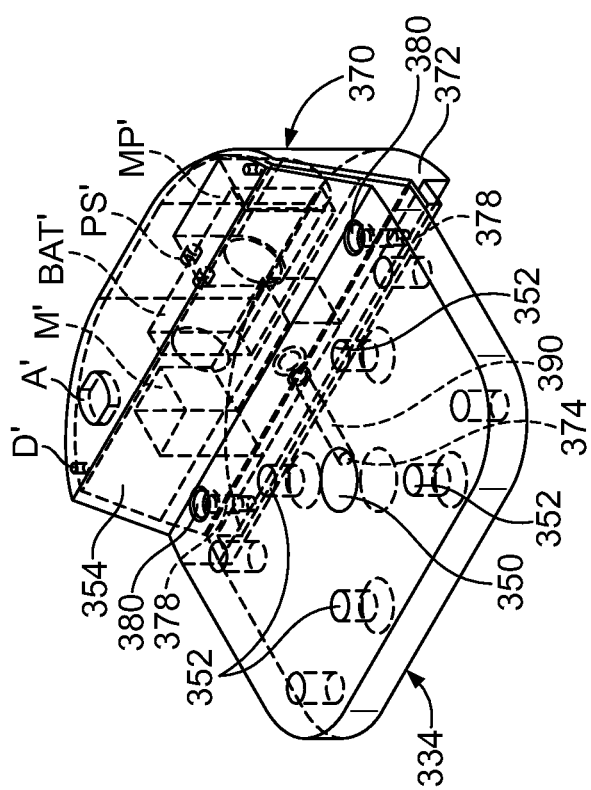
FIG. 4H is a simplified upper perspective view of an upper compression member of the pump system shown in FIG. 4A and further including an electrically activated pump that is shown with a layout of the major components.
Figure 4G:
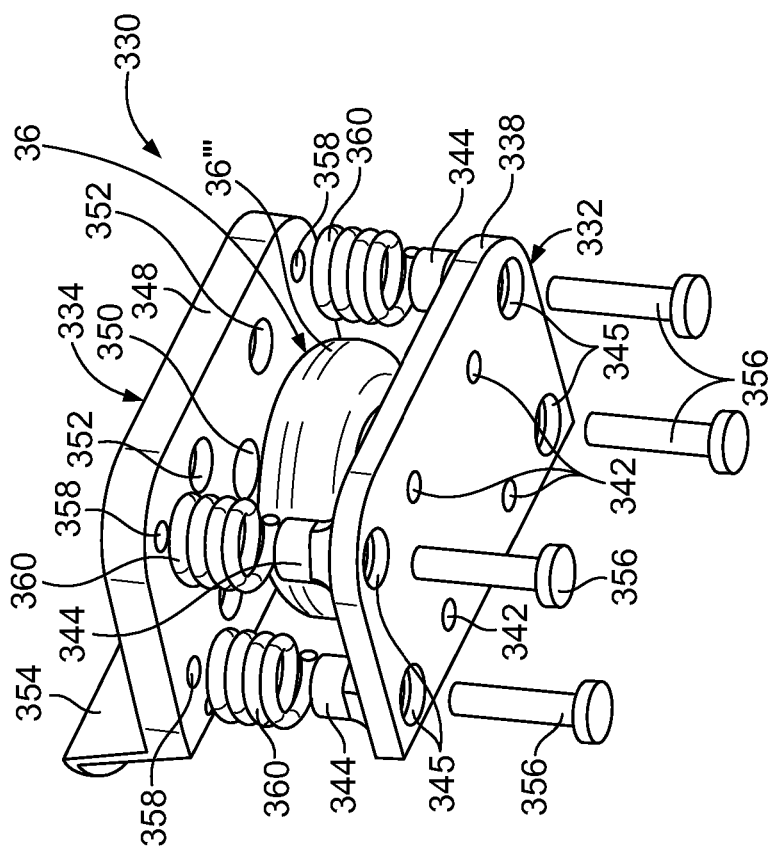
FIG. 4G is a lower rear perspective partially exploded view of the pump system shown in FIG. 4A.

Turning to FIGS. 4A-4H, a fourth example is provided, with the example initially including only a mechanically activated pump in FIGS. 4A-4G, and then in FIG. 4H showing further coupling to and inclusion of an electrically activated pump to form a modular, hybrid pump system.

FIG. 4A shows a simplified side view of a prosthetic device or limb 302 in the form of a prosthetic limb for a transfemoral amputee. The prosthetic device 302 generally includes a socket 4, a fourth example pump system 306, a knee joint 8, a pylon 10 and a prosthetic foot 12. The socket 4 has an upper end 18 that is open and is adapted to receive a transfemoral residual limb, with a lower end 20 that includes a port (not shown) in fluid communication with the pump system 306. It will be appreciated that aside from the pump system 306, the other components of the prosthetic limb 302 are the same as those of the previously described prosthetic limb 2.

FIG. 4B incorporates in a prosthetic device 302' the same components as shown in the simplified side view of a prosthetic device or limb 2', in the form of a prosthetic limb for a transtibial amputee. The prosthetic device 302' generally includes a socket 4', the fourth example pump system 306, a pylon 10' and a prosthetic foot 12. The socket 4' has an upper end 18' that is open and is adapted to receive a transtibial residual limb, with a lower end 20' that includes a port (not shown) in fluid communication with the pump system 306.

The disclosure provided previously relating to the sockets 4, 4' and other components of prosthetic devices apply to and will not be repeated for this fourth example. Thus, though not shown in the simplified drawings, it will be understood that the prosthetic devices 302, 302' would include mounting flanges or other hardware to accommodate mounting of the pump system 306 to the socket 4, 4' and to the upper end of the knee joint 8 or pylon 10'. Nevertheless, the fourth example prosthetic devices 302, 302' also embody low profile, inline structures with a pump system 306 that may be incorporated into a reduced package height, as discussed with the other examples. This would permit fluid connection of the pump system 306 to the lower end 20, 20' of the socket 4, 4', and may eliminate the need for external tubing, having the advantages of such previously noted with respect the first example.

A fourth example pump system 306 may be seen in various views within FIGS. 4C-4H and includes at least a mechanically activated pump 330. As shown in FIG. 4H, the fourth example also may include an electrically activated pump 370. The mechanically activated pump 330 and electrically activated pump 370 may be connected within a fluid circuit 390, a portion of which is shown, but which is connected to and adapted to evacuate air from the socket 4, 4' in a similar manner to that shown in the first example, thereby forming a particularly advantageous modular, hybrid pump system. The evacuation of air from the socket 4, 4', provides vacuum engagement between the prosthetic device 2, 2' and a respective transfemoral or transtibial residual limb. It also will be appreciated that with a pump system that includes a mechanically activated pump 330, the pump system alternatively could be configured for periodic use with a separate hand operated pump to establish initial air evacuation.

The hybrid pump system of this fourth example provides a compact, low profile, inline structure, and takes advantage of space provided at the front of the knee. As may be seen in FIGS. 4C-4H, the mechanically activated pump 330 of the fourth example pump system 306 includes a first compression member 332 coupled to a second compression member 334, with the compressible bladder 36 of the first example being disposed therebetween. The first and second compression members 332, 334 preferably are constructed of relatively light weight, generally rigid materials, such as discussed with respect to the first example.

The first compression member 332 includes a generally planar central body 338 having a central recess (not shown), spaced apart mounting apertures 342, and extensions 344 having bores 345 therethrough and being generally perpendicular to the central body 338. The second compression member 334 includes a generally planar central body 348 having a central aperture 350, spaced apart mounting apertures 352, and an extension in the form of a flange 354 that extends upward and forward from the central body 348. The first compression member 332 is coupled to the second compression member 334 via coupling elements that include four respective fastener pins 356 that may be connected to the second compressible member 334 at apertures 358, such as by press fit or other suitable means of connection, and that slide within the bores 345 of the extensions 344 of the first compression member 332. This coupling configuration provides for translation of the second compression member 334 relative to the first compression member 332. While the coupling elements may be of a different configuration and size, the mechanically activated pump 330 should provide sufficient structural integrity and stability to maintain a consistent and predictable gait and resistance to torsional inputs, such as a twisting motion after planting a step. Optional springs 360 may be placed around the extensions 344 and extend between and first and second compression members 332, 334, tending to bias them toward a spaced apart position. Use of the springs 360 may assist in providing consistent operation and feedback to the user.

The compressible bladder 36 and its associated valving may be particularly effective in this example, as well, in light of the relatively short height, and nearly continuous generally planar upper and lower surfaces that are connected to the radially bulging outer sidewall 36'''. As with the prior examples, the outer sidewall defines an outer perimeter of the compressible bladder 36 and such a configuration for a compressible bladder 36 may permit greater capacity and potential efficiency, within a given overall diameter, when compared to a compressible bladder having an enlarged passage through the center to accommodate a tubular pylon-like telescopic structure. This fourth example similarly has all of the coupling elements disposed about an outer perimeter that is defined by the sidewall 36''' of the compressible bladder 36, such that the coupling elements are at or beyond the outer perimeter of the compressible bladder 36. This permits a shorter pump height and location of the pump system 306 above the knee in a transfemoral configuration, which in turn, may permit a relatively large overall diameter and capacity for the compressible bladder.

As noted previously, the compressible bladder 36 may be constructed of one or more materials and in a manner that will tend to expand or return to its original non-compressed state, thereby separating the first and second compression members 332, 334. However, the optional springs 360 are intended to ensure rebound and expansion of the compressible bladder 36 during repeated telescopic compression movements that occur during walking or isolated bouncing-type movements. Also, as previously noted, it will be appreciated that many configurations of compression members, compressible bladders and coupling elements may be utilized to couple a first compressible member to a second compressible member, and optional spring assemblies may include alternative spring forms, including for example, a leaf spring, or coiled torsion springs having opposed arms and being positions to bias the first and second compression members 332, 334 to a spaced apart position. Given the number of coupling elements and their spaced arrangement, it is believed that a central, relatively long and large tubular telescopic assembly need not be required, and that the shorter, thinner fastener pins 356 sliding within the bores 345 of the extensions 344 will provide for proper alignment and smooth translational movement.

The first and second compression members 332, 334 and compressible bladder 36 utilize a fluid circuit that would be comparable to those previously described to evacuate air from the socket 4, 4' of the prosthetic devices 302, 302'. As noted, the compressible bladder 36 includes an intake valve, and it is able to communicate through an aperture 350 in the second compression member 334, and an output valve is vented to the atmosphere to expel air that has been evacuated from the socket 4, 4' by the pump system 306.

In the fourth example, the electrically activated pump 370 is positioned essentially above and forward of the knee joint 8 or the pylon 10', connected to the flange 354 of the second compression member 334 of the mechanically activated pump 330. As may be seen in a simplified manner in FIG. 4H, the electrically activated pump 370 includes a housing 372 having an inlet valve 374 in communication with the central aperture 350 of the second compression member 334 for fluid connection to the socket 4, 4', and an output valve (not shown) that is vented to the atmosphere to expel air that has been evacuated from the socket 4, 4' by the pump system 306. The housing 372 also includes mounting bores 378 that receive fasteners (not shown) through passages 380 in the central body 348 of the second compression member 334 to connect the electrically activated pump 370 to the mechanically activated pump 330. It will be appreciated that the electrically activated pump may be equipped with alternative valving and operative features, as desired. Also, the housing of the electrically activated pump could be configured to be connected to the mechanically activated pump in an alternative manner, such as for example, in the stacked arrangement shown in the first three examples, just as any of those examples could have utilized a side mounting of their respective electrically activated pumps, such as in the manner shown with the fourth example or in an alternative configuration that places the electrically activated pump outside of the outer perimeter of the compressible bladder. It also will be appreciated that an additional reduction in height may be achieved if the circuitry is positioned along the outer perimeter of the first and/or second compression member.

As may be appreciated in FIG. 4H, the electrical components of the electrically activated pump 370 are shown in a simple layout and it will be understood that they have similar basic functions and connection configurations those described for the first example pump system 6 and which also would apply to the other examples. It will be appreciated that the components may be configured and connected in fluid communication by conventional means, such as by suitable tubing, and/or may be configured and connected electrically by conventional means, such as by suitable wires, leads or other circuitry, so as to meet the needs and satisfy the design specifications and constraints within of a particular implementation. In this fourth example, within the housing 372 of the electrically activated pump 370 is a microcontroller M' that includes a circuit board and is connected to a motorized pump MP', a pressure sensor PS', and a battery BAT'. A user interface A', in the form of an on/of button, is located along the top of the flange 354 and is connected to the microcontroller M'. An optional serial data port D' may be utilized to interact with the microcontroller M', such as to track and record the operating conditions of the pump system 306, for diagnostic and historical monitoring purposes.

As described with respect to the first example and would apply to the other examples, a further user interface, such as in the form of a wireless remote control device or other devices may be utilized, as previously described. In addition, the battery BAT' may be similar to that which was described previously for the other examples.

It will be appreciated that, with inclusion of an electrically activated pump 370, the pump system 306 may present a hybrid, modular system that can be utilized in a number of ways to evacuate air from a socket 4, 4'. Schematics provided for the first example, as well as the associated description, may be referred to and similarly apply to the means of operation and methods of use of the fourth example pump system 306 to establish and maintain an evacuated chamber in the socket 4, 4' of a prosthetic device 302, 302', whether the mechanically activated pump 330 is used alone, or is paired with the electrically activated pump 370 to provide a hybrid pump system.

It will be appreciated that a pump system for use in suspension of a prosthetic device from a residual limb in accordance with the present disclosure may be provided in various configurations. Any variety of suitable materials of construction, configurations, shapes and sizes for the components and methods of connecting the components may be utilized to meet the particular needs and requirements of an end user. It will be apparent to those skilled in the art that various modifications can be made in the design and construction of such pump systems without departing from the scope or spirit of the claimed subject matter, and that the claims are not limited to the preferred embodiments illustrated herein.

What is claimed is:

1. A pump system for use in suspension of a prosthetic device from a transtibial residual limb comprising:
   a mechanically activated pump having pumping action that requires a mechanical input via movement of the prosthetic device and having a first compression member coupled to a second compression member;
   a compressible bladder disposed between the first and second compression members;
   coupling elements that engage and couple together the first and second compression members, wherein all of the coupling elements are disposed about an outer perimeter of the compressible bladder; and
   a separate electrically activated pump having an electrical power source and pumping action that requires an electrical input from the electrical power source, wherein the electrically activated pump is coupled within a fluid circuit with the compressible bladder and the mechanically activated pump.

2. The pump system in accordance with claim 1, wherein the fluid circuit is configured to provide vacuum engagement with the transtibial residual limb.

3. The pump system in accordance with claim 2, wherein the pump system is incorporated into a prosthetic device that further comprises a socket that is configured to receive the transtibial residual limb and the fluid circuit is connected to the socket.

4. The pump system in accordance with claim 1, wherein the first compression member is pivotally coupled to the second compression member.

5. The pump system in accordance with claim 1, wherein the first compression member translates relative to the second compression member.

6. The pump system in accordance with claim 1, wherein the electrically activated pump is disposed outward from the outer perimeter of the compressible bladder.

7. The pump system in accordance with claim 1, wherein the electrical power source further comprises a battery.

8. The pump system in accordance with claim 7, wherein the battery is rechargeable.

9. A hybrid pump system that includes a prosthetic device that is adapted for suspension from a transtibial residual limb comprising:
   a prosthetic device having a transtibial residual limb receiving socket;
   a mechanically activated pump having pumping action that requires a mechanical input via movement of the prosthetic device;
   a separate electrically activated pump having an electrical power source and pumping action that requires an electrical input from the electrical power source;

the mechanically activated pump and electrically activated pump being connected within a fluid circuit that evacuates air from the transtibial residual limb receiving socket; and wherein the mechanically activated pump further comprises a first compression member coupled to a second compression member and an elastomeric member disposed between the first and second compression members and being in fluid communication with the fluid circuit.

10. The hybrid pump system in accordance with claim 9, wherein the electrical power source further comprises a battery.

11. The hybrid pump system in accordance with claim 10, wherein the battery is rechargeable.

12. The hybrid pump system in accordance with claim 9, wherein the elastomeric member further comprises a compressible bladder.

13. The hybrid pump system in accordance with claim 9, wherein the first compression member is pivotally coupled to the second compression member.

14. The hybrid pump system in accordance with claim 9, wherein the first compression member translates relative to the second compression member.

15. The hybrid pump system in accordance with claim 9, wherein the electrically activated pump is disposed above or below the mechanically activated pump.

16. The pump system in accordance with claim 9, wherein the electrically activated pump is disposed outward from the outer perimeter of the compressible bladder.

17. A hybrid pump system that includes a prosthetic device that is adapted for suspension from a transtibial residual limb comprising:
 a prosthetic device having a transtibial residual limb receiving socket;
 a mechanically activated pump having pumping action that requires a mechanical input via movement of the prosthetic device;
 a separate electrically activated pump having an electrical power source and pumping action that requires an electrical input from the electrical power source;
 the mechanically activated pump and electrically activated pump being connected within a fluid circuit that evacuates air from the transtibial residual limb receiving socket; and
 wherein the mechanically activated pump further comprises a first compression member coupled to a second compression member, an elastomeric element disposed between the first and second compression members and being in fluid communication with the fluid circuit, and coupling elements engaging and coupling together the first and second compression members, wherein all of the coupling elements are disposed about an outer perimeter of the elastomeric element.

18. The hybrid pump system in accordance with claim 17, wherein the fluid circuit is in communication with the socket and the elastomeric element of the mechanically activated pump, and the mechanically activated pump evacuates air from the socket when the prosthetic device is used to walk.

19. The hybrid pump system in accordance with claim 17, further comprising a controller and wherein the fluid circuit and controller are configured to evacuate air from the socket by operating the electrically activated pump when the prosthetic device is not being used to walk and the air pressure within the socket is outside of a preselected range of values.

20. The hybrid pump system in accordance with claim 17, further comprising a controller and wherein the fluid circuit and controller are configured to evacuate air from the socket by operating the electrically activated pump when the transtibial residual limb is initially received within the socket.

21. The hybrid pump system in accordance with claim 17, wherein a preselected level of vacuum within the socket is maintained by operation of the mechanically activated pump.

22. The hybrid pump system in accordance with claim 17, wherein a preselected level of vacuum within the socket is maintained by operation of the electrically activated pump.

23. The hybrid pump system in accordance with claim 17, wherein the first compression member is pivotally coupled to the second compression.

24. The hybrid pump system in accordance with claim 17, wherein the first compression member translates relative to the second compression member.

25. The hybrid pump system in accordance with claim 17, wherein at least one spring is disposed between the first compression member and the second compression member.

26. The hybrid pump system in accordance with claim 25, wherein the at least one spring biases the first compression member toward a position spaced apart from the second compression member.

* * * * *